United States Patent [19]

Erpenbach et al.

[11] 4,012,439

[45] Mar. 15, 1977

[54] CONTINUOUS PRODUCTION OF n-BUTYLACRYLATE FREE FROM DIBUTYLETHER

[75] Inventors: Heinz Erpenbach, Surth near Cologne; Klaus Gehrmann, Erftstadt-Lechenich; Herbert Joest, Erftstadt-Liblar; Peter Zerres, Erftstadt-Friesheim, all of Germany

[73] Assignee: Hoechst Aktiengesellschaft, Frankfurt am Main, Germany

[22] Filed: Oct. 14, 1975

[21] Appl. No.: 622,263

[30] Foreign Application Priority Data

Oct. 19, 1974 Germany .......................... 2449811

[52] U.S. Cl. .......................................... 260/486 R
[51] Int. Cl.² .......................................... C07C 69/54
[58] Field of Search .............................. 260/486 R

[56] References Cited

UNITED STATES PATENTS 3,278,585  10/1966  Baker et al. .................. 260/486 R

FOREIGN PATENTS OR APPLICATIONS 841,521    7/1960  United Kingdom ............... 260/486
1,003,007  9/1965  United Kingdom ............... 260/486

OTHER PUBLICATIONS

Levesque, C. L. et al., Industrial and Engineering Chem., vol. 40, No. 1, pp. 96–99, Jan. 1948.

*Primary Examiner*—Paul J. Killos
*Attorney, Agent, or Firm*—Connolly and Hutz

[57] ABSTRACT n-Butylacrylate is produced by reacting acrylic acid with n-butanol in liquid phase in contact with an acid cation exchanger as a catalyst.

To this end, the acrylic acid and butanol are reacted in a molar ratio from 1:1 to 1:2.5, at 80° to 130° C, under a pressure from 3 to 15 atmospheres gauge, and for 20 – 90 minutes.

1 Claim, 1 Drawing Figure

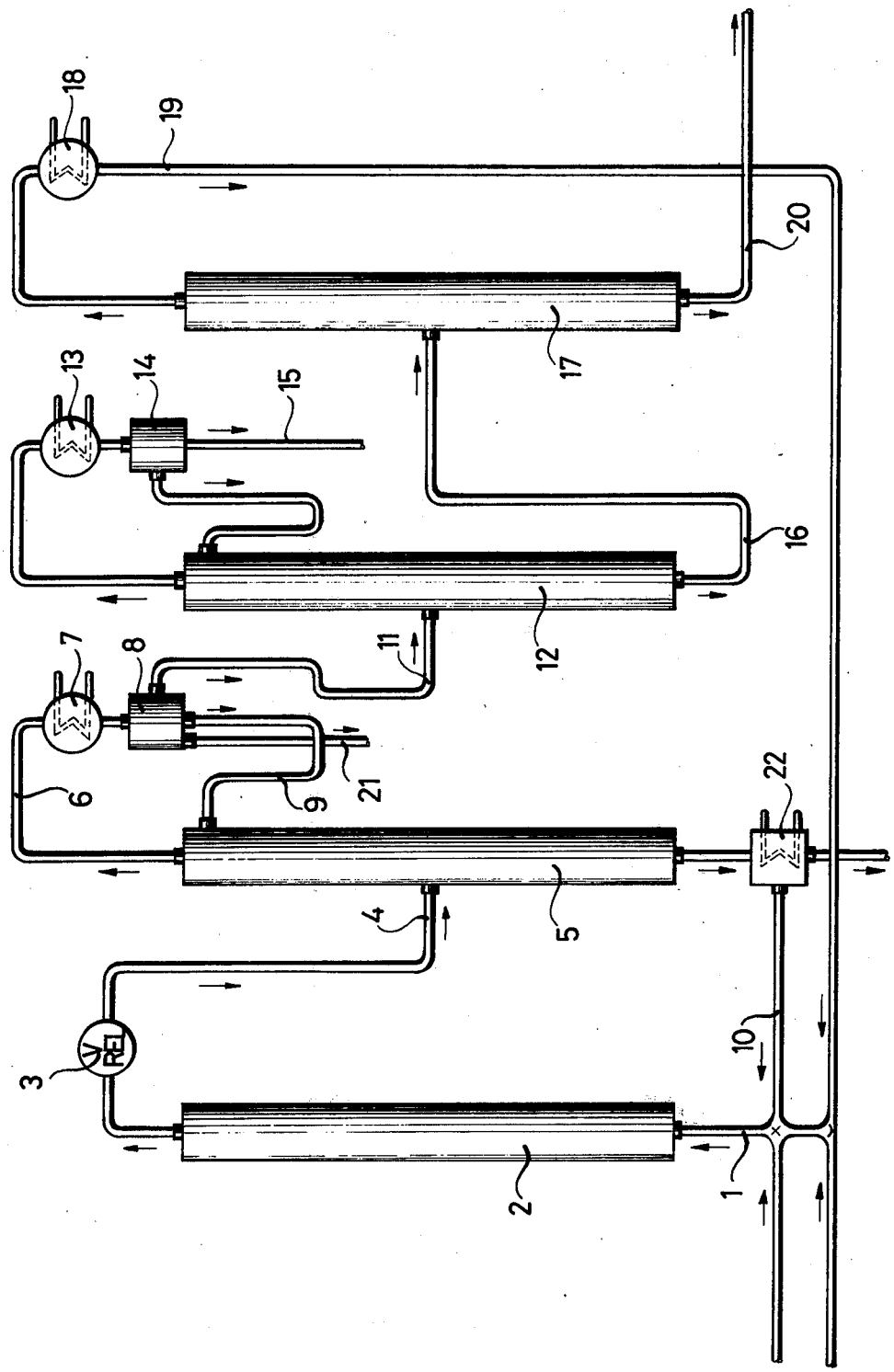

CONTINUOUS PRODUCTION OF n-BUTYLACRYLATE FREE FROM DIBUTYLETHER

Various processes for making n-butylacrylate (acrylic acid n-butylester), wherein acrylic acid is reacted with n-butanol in liquid phase, at elevated temperature and in the presence of an acid cation exchanger as a catalyst have already been described in the art, e.g. in German Patent Specification "Offenlegungsschrift" No. 2 226 829. These processes are more particularly concerned with equilibrium reactions, wherein the equilibrium constant is the factor which critically determines the conversion rate of the acid or alcohol to the ester. As a result, it is necessary for unreacted starting material to be separated from the ester produced and to be recycled to the reaction zone. This is an operation which entails considerable difficulties in reducing the process to practice.

To increase the acrylic acid conversion to the ester, it has been proposed, for example, to use butanol in a large excess with respect to acrylic acid, or to remove the reaction water by azeotropic distillation or to extract the ester with a solvent during the reaction. This is, however, not satisfactory as it is necessary for an important excess of butanol to be recovered, or for the distillation aid or the solvent extractant to be separated. In addition to this, a considerable quantity of undesirable dibutylether by-product, which has the same boiling point as the butylester, is obtained.

The present invention now provides a process which is free from the disadvantages described hereinabove and which comprises reacting acrylic acid and butanol in a molar ratio within the range 1:1 and 1:2.5, at temperatures within the range 80° and 130° C, under a pressure within the range 3 and 15 atmospheres gauge, and for periods within the range 20 and 90 minutes.

A preferred embodiment of the present process comprises: introducing continuously acrylic acid and n-butanol into a reaction zone being filled with an acid cation exchanger; delivering the resulting esterification mixture to a first distillation zone, distilling off near the head of the first distillation zone a ternary mixture consisting of butylacrylate, butanol and water, condensing the mixture and separating it into an organic phase and an aqueous phase, recycling the bulk of the aqueous phase to the head of the first distillation zone and removing the aqueous phase balance portion; removing concentrated acrylic acid from the bottom portion of the first distillation zone, distilling off higher boiling fractions and recycling the acrylic acid to the reaction zone; delivering the organic phase recovered from distillate of the first distillation zone to a second distillation zone, distilling off near the head of the second distillation zone a ternary mixture consisting of butylacrylate, butanol and water, condensing the mixture and separating it into an organic phase and an aqueous phase, recycling the organic phase to the head of the second distillation zone and removing the aqueous phase; delivering base product obtained in the second distillation zone and consisting of butylacrylate and butanol to a third distillation zone, distilling off near the head of the third distillation zone a butanol/butylacrylate-azeotrope, condensing the azeotrope and recycling it to the reaction zone, and removing pure n-butylacrylate through the bottom portion of the third distillation zone.

The acid cation exchanger which should preferably be used is a polystyrene/sulfonic acid based cation exchanger resin.

With respect to the esterification reaction, it is advantageous for it to be effected at temperatures within the range 85° and 125° C. Higher temperatures have been found to promote the formation of dibutylether and polymerization and thereby to affect the catalyst performance, whilst lower temperatures effect a considerable reduction of the reaction velocity.

The reaction should preferably be effected under the pressure necessary to maintain the liquid phase under the reaction conditions selected. A reaction pressure within the range 5 and 10 atmospheres gauge has very beneficial effects on the catalyst performance.

The esterification reaction and distillative separation should conveniently be effected in the presence of a suitable polymerization inhibitor, which may be selected, for example, from hydroquinone, hydroquinonemonomethylether, p-benzoquinone, phenothiazine or methylene Blue, and used in admixture with air, if desired.

With respect to the butanol starting material, it is allowable for it to contain some water or butylacrylate. The acrylic acid and butanol are, however, required to be present in the reaction zone in a molar ratio within the range 1:1 and 1:2.5, preferably 1:1.3 and 1:2. Lower ratios effect a reduction of the reaction velocity and of the conversion, while higher ratios effect the formation of undesirable dibutylether.

A preferred embodiment of the process will now be described by way of example with reference to the accompanying flow scheme.

As can be seen, a reactor 2 having the catalyst secured therein is supplied with acrylic acid and n-butanol through line 1. The quantity of starting material supplied determined the quantity of resulting esterification mixture, which flows through a pressure-retaining valve 3 and which is delivered through line 4 to first distillation column 5. A ternary mixture consisting of butylacrylate, butanol and water is the distillate travelling through line 6 at the head of column 5, which is operated under a pressure of 100–760 mm Hg and at a temperature of 46°–92° C. The distillate is condensed in condenser 7 and separated in separator 8 into an organic phase and an aqueous phase, of which about 97% is preferably recycled to the head of column 5, through line 9, and of which about 3% is preferably removed, through line 21. The base of column 5, which is operated under a pressure of 100–760 mm Hg at a temperature of 65°–140° C, contains acrylic acid of about 85 weight % strength. The acid is distillatively freed from higher boiling fractions in an evaporator 22, which is operated under a pressure of 20–200mm Hg and at a temperature of 40°–95° C, and recycled to reactor 2, through line 10 and 1.

The organic phase, which consists of butylacrylate, butanol and about 6 weight % of water and accumulates in separator 8, is delivered to second distillation column 12, through line 11. A ternary mixture of butylacrylate, butanol and water is removed at the head of column 12 under a pressure of 100–760 mm Hg and at a temperature of 46°–92° C. The mixture is condensed in condenser 13 and separated into two phases in separator 14, of which the organic phase is refluxed to column 12, whereas the aqueous phase is removed, through line 15. Anhydrous base product consisting of butylacrylate and butanol is removed under a pressure of 100–760 mm Hg and at a temperature of 65°–140° C from the base of column 12 and delivered to third distillation column 17, through line 16. Column 17 is operated under a pressure of 20–760 mm Hg, at a head temperature of 39°–117° C and a base temperature of 45°–47° C, and used to effect separation therein into a butanol/butylacrylate-azeotrope (head product), which is condensed in condenser 18 and recycled to esterification reactor 2, through lines 19 and 1, and into pure butylacrylate (base product) which is discharged through line 20.

Polymerization of the material in the three columns is inhibited by means of a polymerization inhibitor which is added thereto.

EXAMPLE 1

The reactor 2 was a cylindrical jacketed stainless steel reactor. It had an internal diameter of 25 mm, a length of 850 mm and was steam-heated. Placed in the interior of the reactor was 250 cc (155 g) of a commercially available acid cation exchanger (AMBERLYST 15, a product of Rohm and Haas) as a catalyst.

The reactor was supplied with the starting materials, which were introduced from below and travelled upwardly therein. Pressure-retaining valve 3 at the reactor outlet was used to establish the working pressure. The system was supplied per hour with 83 g (1.15 mol) of fresh acrylic acid, 85 g (1.15 mol) of fresh n-butanol and with unreacted recycle product, which travelled through line 1. In other words, reactor 2 was charged per hour with altogether 300 g of a mixture consisting of 98.5 g (32.8 weight %) of acrylic acid (1.37 mol), 172 g (57.3 weight %) of n-butanol (2.33 mol) and 29.5 g (9.9 weight %) of n-butylacrylate (acrylic acid n-butylester; 0.23 mol). The molar ratio of acrylic acid to n-butanol accordingly was 1:1.7. 84.3% of the acrylic acid was converted in reactor 2 at a reaction temperature of 120° C, under a pressure of 7 atmospheres gauge and within 45 minutes. 300 g/h of reaction product containing 174.5 g (1.364 mol) of n-butylacrylate, 15.5 g (0.215 mol) of acrylic acid, 87 g (1.175 mol) of butanol and 20 g (1.134 mol) of water as well as 3 g of residue was removed through pressure-retaining valve 3 and introduced through line 4 approximately into the center portion of first distillation column 5, which was operated under a pressure of 200 mm Hg and at a temperature of 88° C. 18.5 g/h of base product containing 84 weight % of acrylic acid and 4 weight % of water was removed, distillatively freed from residue in evaporator 22 under a pressure of 50 mm Hg and at 56° C, and recycled to reactor 2 through line 10. The head product obtained at 63° C was a ternary mixture of butylacrylate, butanol and water, which was condensed and separated into two phases. 97% (= 100 g/h) of the aqueous phase was recycled through line 9 to column 5 to effect formation of the ternary mixture therein, and 3% (= 3.5 g/h) was removed from the system through line 21. 278 g/h of organic phase, which was free from acrylic acid and contained 62.7 weight % of butylacrylate, 31.3 weight % of butanol and 6 weight % of water, was introduced through line 11 approximately into the center portion of second distillation column 12. The ternary mixture which went over at a head temperature of 62° C under a pressure of 150 mm Hg was condensed and gave two phases, of which the organic phase (from column 12) was refluxed, and of which the aqueous phase (16.5 g) was removed through line 15. 261.5 g of anhydrous base product was discharged at 83° C and introduced through line 16 approximately into the center portion of third distillation column 17. 116.5 g/h of an azeotropic mixture of 74.5 weight % of butanol and 25.5 weight % of butylacrylate was obtained as the head product at 53° C under a pressure of 50 mm Hg. It was recycled to reactor 2 through lines 19 and 1. The column base product, which was n-butylacrylate free from dibutylether, was obtained at 83° C at a hourly rate of 143 g (1.12 mol). This corresponded to a yield of 97.4%, based on the acrylic acid which underwent conversion. The catalyst performance was 923 g of n-butylacrylate per kg of catalyst per hour. The material in each of the three columns was stabilized by means of 0.1 weight % of hydroquinone, based on the weight of the liquid phase. The gas phase was stabilized additionally in each of the columns by means of air.

EXAMPLE 2

The apparatus was the same as that described in Example 1. The pressure was reduced down to 3 atmospheres gauge while the other parameters, namely the 120° C reaction temperature and the acrylic acid to n-butanol molar ratio of 1:1.7 remained unchanged. 290 g of a mixture consisting of 57 weight % of n-butanol, 32.6 weight % of acrylic acid and 10.4 weight % of n-butylacrylate was put through in reactor 2. 81.4% of the acrylic acid underwent conversion. 290 g/h of reaction product containing 55.8 weight % of butylacrylate, 29.9 weight % of butanol, 6.55 weight % of water, 6.05 weight % of acrylic acid and 1.7 weight % of residue was discharged from reactor 2. 130 g/h of pure butylacrylate was obtained. This corresponded to a yield of 95%, based on the acrylic acid which underwent conversion. The catalyst performance was 838 g of butylacrylate per kg of catalyst per hour.

EXAMPLE 3

The apparatus was the same as that described in Example 1. The reaction temperature was 120° C, the acrylic acid to n-butanol molar ratio was 1:1.7 and the working pressure was increased to 15 atmospheres gauge. 280 g/h of a mixture consisting of 32.8 weight % of acrylic acid, 57.3 weight % of butanol and 9.9 weight % of butylacrylate was put through in reactor 2. The acrylic acid conversion rate was 84.7%. 280 g/h of reaction product (this corresponded to the quantity of starting material used) containing 57.8 weight % of butylacrylate, 5 weight % of acrylic acid, 28.9 weight % of n-butanol, 6.8 weight % of water and 1.4 weight % of residue, was removed. The material was worked up and 134 g of pure n-butylacrylate was obtained. This corresponded to a yield of 96.4%, based on the acrylic acid which underwent conversion. The catalyst performance was 866 g of butylacrylate per kg of catalyst per hour.

EXAMPLE 4

The conditions were the same as those described in Example 1, but the reaction temperature was increased from 120° to 130° C. The reactor was charged with 310 g/h of a mixture consisting of 32.7 weight % of acrylic acid, 57.2 weight % of n-butanol and 10.1 weight % of butylacrylate. 83.2% of the acrylic acid underwent conversion. 310 g of reaction product consisting of 175 g of butylacrylate, 90 g of n-butanol, 21 g of water, 17 g of acrylic acid and 7 g of residue was discharged. 143 g/h of pure butylacrylate free from dibutylether was obtained. This corresponded to a yield of 95.7%, based on the acrylic acid which underwent conversion. The catalyst performance was 923 g of butylacrylate per kg of catalyst per hour.

EXAMPLE 5

The conditions were the same as those described in Example 1, but the reaction temperature was reduced from 120° C down to 85° C. The reactor was charged with 316 g/h of a mixture consisting of 100 g of acrylic acid, 175 g of n-butanol and 41 g of n-butylacrylate. An identical quantity of reaction product consisting of 136 g of butylacrylate, 46 g of acrylic acid, 120 g of n-butanol, 13 g of water and 1 g of residue was obtained. 54 g of the acrylic acid underwent conversion. 93 g/h of pure butylacrylate free from dibutylether was obtained. This corresponded to a yield of 97%, based on the acrylic acid which underwent conversion. The catalyst performance was 600 g of butylacrylate per kg of catalyst per hour.

EXAMPLE 6

The conditions were the same as those described in Example 1, but acrylic acid and n-butanol were used in the molar ratio of 1:1. The reactor was supplied with 297 g/h of a mixture consisting of 138 g of acrylic acid, 142 g of n-butanol and 17 g of butylacrylate. An identical quantity of reaction product consisting of 173 g of butylacrylate, 46 g of acrylic acid, 50 g of butanol, 22 g of water and 6 g of residue was discharged. 66.7% of the acrylic acid underwent conversion. 154 g/h of pure butylacrylate free from dibutylether was obtained. This corresponded to a yield of 94.1%, based on the acrylic acid converted. The catalyst performance was 933 g of butylacrylate per kg of catalyst per hour.

EXAMPLE 7

The conditions were the same as those described in Example 1, but acrylic acid and n-butanol were used in the molar ratio of 1:2.5. The catalyst zone was fed with 325 g/h of a mixture consisting of 78 g of acrylic acid, 202 g of n-butanol and 45 g of butylacrylate. 325 g of reaction product containing 163 g of butylacrylate, 10 g of acrylic acid, 132 g of butanol, 17 g of water and 3 g of residue was obtained. 87.3% of the acrylic acid underwent conversion. The material was worked up and 116 g/h of pure butylacrylate free from dibutylether was obtained. This corresponded to a yield of 96.1%, based on the acrylic acid converted. The catalyst performance was 749 g of butylacrylate per kg of catalyst per hour.

COMPARATIVE EXAMPLE A

The reaction temperature was increased to 140° C and was accordingly outside the temperature range described herein. The molar ratio of acrylic acid to n-butanol of 1:1.7 and the working pressure of 7 atmospheres gauge used in Example 1 remained unchanged. 102 g of acrylic acid and 178 g of n-butanol were passed per hour through the reactor. The acrylic acid conversion rate was 85.1%. 280 g of reaction product containing 52.9 weight % of butylacrylate, 5.35 weight % of acrylic acid, 31.45 weight % of n-butanol, 7.85 weight % of water, 0.35 weight % of dibutylether and 2.1 weight % of residue was obtained. The butanol/-butylacrylate-azeotrope obtained at the head of third distillation column 17 contained 0.5 weight % of dibutylether and was, therefore, not recycled to the reactor, 146 g/h, including the butylacrylate fraction contained in the azeotrope, of butylacrylate contaminated with 0.3 weight % of dibutylether was obtained. This corresponded to yield of 94.4%, based on the acrylic acid converted. The catalyst performance was 942 g of butylacrylate per kg of catalyst per hour.

As can be seen, dibutylether is obtained as an undesirable by-product if the reaction is carried out at a temperature outside the temperature range of the present invention.

COMPARATIVE EXAMPLE B

Acrylic acid and n-butanol were used in a molar ratio of 1:3 so as to be outside the molar ratio described herein. The working pressure was 7 atmospheres absolute and the reaction temperature was 120° C. The reactor was supplied with 280 g/h of a feed mixture consisting of 24.5 weight % of acrylic acid and 75.5 weight % of n-butanol. The acrylic acid conversion rate was 91.3%. 280 g/h of reaction product containing 37.8 weight % of butylacrylate, 2.1 weight % of acrylic acid, 52.1 weight % of n-butanol, 5.7 weight % of water, 0.4 weight % of dibutylether and 1.8 weight % of residue was obtained. The butylacrylate/butanol-azeotrope coming from the third distillation column 17 contained 0.4 weight % of dibutylether and was, therefore, not recycled. 105 g/h, including the butylacrylate fraction in the azeotrope, of butylacrylate contaminated with 0.4 weight % of dibutylether was obtained. This corresponded to a yield of 94%, based on the acrylic acid converted. The catalyst performance was 678 g of butylacrylate per kg of catalyst per hour.

As can be seen, dibutylether is obtained as an undesirable by-product and the catalyst performance is impaired by using n-butanol in a molar excess beyond the upper limiting value in the molar ratio described herein.

We claim:

1. In the process for making n-butylacrylate by reacting acrylic acid with n-butanol in liquid phase in contact with an acid cation exchanger as a catalyst, the improvement, which comprises continuously introducing into, and reacting in, a reaction zone acrylic acid and n-butanol in a molar ratio within the range 1:1 and 1:2.5, at temperatures within the range 80 and 130° C, under a pressure within the range 3 and 15 atmospheres gauge, and for reaction periods within the range 20 and 90 minutes, the reaction zone being filled with an acid cation exchanger; delivering the resulting esterification mixture to a first distillation zone, distilling off near the head of the first distillation zone a ternary mixture consisting of butylacrylate, butanol and water, condensing the mixture and separating it into an organic phase and an aqueous phase, recycling the bulk of the aqueous phase to the head of the first distillation zone and removing the aqueous phase balance portion; removing concentrated acrylic acid from the bottom portion of the first distillation zone, distilling off higher boiling fractions and recycling the acrylic acid to the reaction zone; delivering the organic phase recovered from distillate of the first distillation zone to a second distillation zone, distilling off near the head of the second distillation zone a ternary mixture consisting of butylacrylate, butanol and water, condensing the mixture and separating it into an organic phase and an aqueous phase, recycling the organic phase to the head of the second distillation zone and removing the aqueous phase; delivering base product obtained in the second distillation zone and consisting of butylacrylate and butanol to a third distillation zone, distilling off near the head of the third distillation zone a butanol/butylacrylate-azeotrope, condensing the azeotrope and recycling it to the reaction zone, and removing pure n-butylacrylate through the bottom portion of the third distillation zone.

* * * * *